United States Patent [19]

Hofacker-Freifrau Von Nostitz

[11] 4,155,890

[45] May 22, 1979

[54] DENTAL PLASTIC

[76] Inventor: Frauke Hofacker-Freifrau Von Nostitz, Allescher Str. 45, München 71, Fed. Rep. of Germany, 8000

[21] Appl. No.: 897,536

[22] Filed: Apr. 18, 1978

[30] Foreign Application Priority Data

Apr. 22, 1977 [DE] Fed. Rep. of Germany ....... 2718017

[51] Int. Cl.$^2$ .................. C08F 20/06; C08F 20/14; C08L 33/08; C08L 33/10
[52] U.S. Cl. .................... 260/23 AR; 32/2; 32/8; 260/998.11
[58] Field of Search ..... 260/23 AR, 998.11, DIG. 36; 32/2; 32/8

[56] References Cited

U.S. PATENT DOCUMENTS

| | | | |
|---|---|---|---|
| 2,234,993 | 3/1941 | Vernon et al. | 32/2 |
| 2,947,716 | 8/1960 | Cornell et al. | 260/998.11 |
| 2,964,486 | 12/1960 | Bernier | 260/23 AR |
| 2,985,605 | 5/1961 | Domanski et al. | 260/23 AR |
| 3,558,540 | 1/1971 | Molnar | 260/23 AR |
| 3,860,556 | 1/1975 | Taylor | 260/998.11 |
| 3,976,611 | 8/1976 | Aloia | 260/23 AR |

FOREIGN PATENT DOCUMENTS

| | | | |
|---|---|---|---|
| 2555184 | 6/1976 | Fed. Rep. of Germany | 260/23 AR |
| 6401531 | 8/1964 | Netherlands | 260/23 AR |
| 484343 | 5/1938 | United Kingdom | 260/DIG. 36 |
| 497179 | 12/1938 | United Kingdom | 260/DIG. 36 |
| 1112987 | 5/1968 | United Kingdom | 260/998.11 |

*Primary Examiner*—Ronald W. Griffin
*Attorney, Agent, or Firm*—Browdy & Neimark

[57] ABSTRACT

Dental plastic, suitable for cold polymerization in the mouth, is formed of a mixture of acrylic polymer dissolved in monomer of methacrylate and/or acrylate of 6 - 10 carbons, to which is added metal soap and, if need be, metal silica and optionally a cross-linking agent.

22 Claims, No Drawings

DENTAL PLASTIC

FIELD OF INVENTION

The invention relates to a material for the manufacture of soft plastic or elastic and/or hard materials for dental-technical, dental-medical, and related purposes, such dental material being based on monomers and polymers (or copolymers and/or mixed polymers) of acrylates and/or methacrylates, and additives, and possibly containing one component of a two-component accelerator or hardening system.

BACKGROUND OF THE INVENTION

The use of acrylic or methacrylic acid esters for dental, medical, and technical purposes, especially for the manufacture of plastic dental prostheses or their linings, when the prosthesis fit has changed in the course of time, as well as their use for taking jaw impressions, etc. is known. It is also known to add additives, such as plastics of other types, cellulose derivatives, natural resins (such as Kopal, Sandarac), paraffin, wax, oil, dye and fillers, to the acrylic or methacrylic acid esters for this purpose. Acrylic or methacrylic acid esters are generally used in the form of a powder, bead, or chip granulate of the polymer or mixed polymers of these compounds dissolved in a liquid monomer, usually methacrylic acid methyl ester, and this solution is caused to harden, possibly with the addition of promoters. This process suffers from several disadvantages.

Dissolving the powder in the liquid is relatively time-consuming. In cold polymerization in a powder-liquid system, it is known that parts of the polymer are easily left undissolved, resulting in a loss of stability and homogeneity of the resultant product. Cold polymers based upon monomeric methyl methacrylate are also harmful to mucous membranes. Moreover, burns can result from processing these cold polymers in the mouth, for example when polymerization is allowed to proceed rapidly. In the manufacture of linings from such monomeric methyl methacrylate solutions, the resultant products do not always have perfectly smooth surfaces and are therefore more likely to be attacked by the microflora in the mouth because they partially adsorb saliva. In addition, such products also suffer from undesirable "shrinkage."

SUMMARY OF THE INVENTION

Objects of the invention therefore are to overcome deficiencies in the prior art, such as noted above; provide improved dentistry; provide for improved dental plastics; provide a material of the type described above which produces smooth odor-free surfaces after it is processed, exhibiting tissue tolerance, sufficient mechanical strength, and freedom from odor and taste, even after being worn for a long time, while simultaneously retaining optimum accuracy of fit over long periods of time. This material must be easily adjustable by slight variations to the desired consistency, for example very hard, soft, or elastic if necessary. According to another aspect of this objective, the material must not contain any monomeric methyl methacrylate, added during cold polymerization.

These objects are achieved by the manufacture of a material of the type described, characterized by the fact that (a) a copolymer or polymer is present as a solution or paste in a monomeric acrylic and/or methacrylic acid ester which is preferably not a lower ester; and the solution or paste (b) contains a metal soap component, and (c) possibly a cross-linking agent.

DETAILED DESCRIPTION OF EMBODIMENTS

The methyl ester of acrylic and/or methacrylic acid may be used as a solvent or dispersant for the homopolymer, copolymer, or mixed polymer component. This embodiment of the invention is used in those applications in which hot polymerization is provided, i.e. complete polymerization does not take place in the patient's mouth itself.

An especially preferred material according to the invention, however, does not contain any significant amount (or in especially advantageous cases, none whatever) of monomeric acrylic acid or methacrylic acid methyl ester, instead using the higher boiling ester derivatives of these acids. In particular, a major content of at least one monomeric acrylic and/or methacrylic acid ester, with 6 to 10 carbon atoms, is used as solvent or dispersant. Examples are 2,3-epoxypropyl-, n- or t-butyl, n-or cyclohexyl-methacrylic acid ester or mixtures of these monomers. The analogous esters of acrylic acid can also be used, it being especially advantageous to use mixtures of the above-mentioned monomeric acrylic acid esters and methacrylic acid esters.

While use of ester derivatives with a total of 6 to 10 carbon atoms is preferred, ester derivatives of acrylic or methacrylic acid can also be used at least in part, whose total number of carbon atoms is less than or more than the range of 6 to 10 carbon atoms considered advantageous, for example, methacrylic acid dodecylester, methacrylic acid triethylene glycol monoethylether, methacrylic acid ethylhexylester, etc.

Finally, an especially advantageous monomer is a reaction product of glycidyl methacrylate and Bisphenol A. A dimethacrylic acid ester of Bisphenol A (for example Diacryl 101 from Akzo-Chemie GmbH, Emmerich, West Germany) is likewise preferred.

The polymers can be basically polyacrylates or methacrylates, including mixed polymers and/or copolymers of the monomers. In addition, certain amounts of plastics of other types, for example polyvinyl chloride, polyvinyl acetate, or polyvinyl alcohol may be present. It is preferable to use a mixture of polymethacrylates with medium molecular weights. Especially advantageous are those polymers, such as polymethylmethacrylate mixtures, which exhibit good solubility properties in the monomer components used and the solvent components also partially present. Such polymethylmethacrylate mixtures of medium molecular weight, which are soluble for example in esters, ketones, chlorinated and aliphatic hydrocarbons, cyclic ethers and the like, and exhibit thermoplastic properties, are commercially available The amount of polymer component in the monomer solution, which may contain additives, can vary within wide limits. Usually, polymer components make up between 10 and 85 wt.%, based on the total composition. The range from 10 to 40% for the weight component of the polymer is especially preferred, based upon the total mass, since especially light liquid-to-pasty and doughy materials are produced, which can be cast, injection molded, mixed with a spatula, or squeezed out and distributed from pressurized containers in the form of a flowing doughy, or pasty material. The mixtures in quantitative amounts of the above-mentioned preferred range, despite the relatively low polymer content, exhibit surprisingly good dimensional stability. Moreover, they also exhibit an outstanding ability to repel water and saliva.

Metal soaps or mixtures thereof are added to solutions or the syrup, pastes, or doughy mixtures made of polymers or mixed polymers in monomer. Alkali silicates or combined alkali metal silicates can be added, these liquid solutions, pastes, or doughy materials being hardenable by adding a catalyst and possibly an accelerator.

Stearates, laurates, oxystearates, palmitates, montanates, oleates, or ricinoleates of metals, such as aluminum, magnesium or calcium, for example, have proven suitable as metal soaps. The alkaline earth soaps are especially preferred. It is important in this regard that the metal soaps be in a finely divided form. A metal soap with especially favorable properties is magnesium stearate, which can be made very finely particulate. Very favorable results have also been achieved with calcium stearate. The amounts of metal soaps or their mixtures used are advantageously 0.1 to 10%, preferably 1.5 to 2.5%, calculated on the basis of the total weight.

Alkali silicates, especially commercially available soluble waterglass compounds, are especially suitable as the metal silicates, and are preferably used in several embodiments of the invention, whereby both sodium and potassium silicates or mixed alkali silicates can be used. Such mixed alkali metal silicates, alkali aluminum silicate, for example, are also very suitable. The amount of such alkali silicates added, preferably employed in the solid or liquid form, is approximately 0.5 to 10%, preferably 1.5 to 5% solids, calculated on the basis of the total volume of the material. In these waterglass preparations, the so-called oil number (cf. Ullmann, Enzyklopadie der Technischen Chemie [Encyclopedia of Chemical Technology], Third Edition, Vol. 13, pp. 742 and 748) must not be more than 26, and an oil number of approximately 22 has proven especially suitable. A typical suitable alkali aluminum silicate contains approximately 60%. $SiO_2$ and between 20 and 25% $Al_2O_3$, in addition to traces of other metal oxides.

The materials according to the invention can contain both metal silicate and metal soaps, whereby especially outstanding dimensional stability and favorable surface-quality properties can be obtained.

By adding the above substances it is possible to improve considerably the toughness, hardness, strength, and surface quality of the polyacrylate or methacrylate materials, and to produce non-porous, tough, non-brittle, shrink-free materials which are tolerated by the mucous membranes and are highly suitable for various applications in dental medicine and technology and for other purposes. It is also possible to manufacture elastic, soft or permanently hard, linings, dental fillings, or even entire dental prostheses as desired, which are admittedly flexible but are non-porous and non-pulverizable, will not shrink, have a smooth, continuous, and hard or elastic surface, and retain this elasticity for a long time. In particular, however, they exhibit optimum accuracy of fit. In this way, the hardness or elasticity can be adjusted at will as needed.

In the event of special demands on the finished dental medical products, it may be advantageous for the materials according to the invention to contain a cross-linking agent. In particular, olefinic dimethacrylates such as ethylene dimethacrylate, propylene dimethacrylate, polyethylene glycol dimethacrylate have proven to be especially suitable as known materials for cross-linking methacrylate or acrylate. It is advantageous for the polyethylene glycol dimethacrylate cross-linking agent which may be added to have a relatively low molecular weight. The cross-linking agent, which is especially suitable for inhibiting the later development of stress cracks, can be added, for example, in amounts of up to 10% based on the total weight.

However, the cross-linking agent can also be added in larger amounts, partially replacing the monomeric methacrylate or acrylate. According to one embodiment of the invention, which is considered especially preferred for certain applications, the monomer component can be replaced nearly or completely by a monomeric cross-linking agent. In the latter case, the polymer component would be dissolved exclusively in monomeric cross-linking agent.

In order to increase the permanence of the materials according to the invention, small amounts of stabilizers or inhibitors can be added to them which inhibit undesired further polymerization of the solution during storage. These substances include for example phenol compounds such as aminophenols dibutylmethyl phenol, or butylhydroxyanisole as well as hydroquinone, pyrogallol, or pyrocatechol. These inhibitors can be added in amounts of approximately 2 to 100 ppm of the material.

Methacrylates usually have a typical bitter aftertaste, which can be a disturbing effect temporarily when fitting protheses or linings. In order to overcome this, sweeteners free of carbohydrates are advantageously added to the material, such as cyclamates, or anticariogenic sugar additives with a carbohydrate base, such as xylite; the mixture of sodium cyclamate with 10% saccharin, known under the trade name of "Natreen", has proven particularly advantageous. Moreover, the usual color additives may be added to the solution.

The catalyst used to harden the acrylate or methacrylate solution can be added essentially in powder form. However, it is advantageous to use it in the form of a solution in a solvent, the solvent being made highly volatile, since it can be dispersed easily and uniformly in the acrylate solution in this manner. Hydroperoxides, such as hydrogen peroxide, tertiary butylhydroperoxide, cumolhydroperoxide, as well as dialkyl and diaralkyl peroxides, ketone peroxides, diacyl peroxides such as dibenzoyl peroxide, or peroxic acids, can be used as catalysts or initiators, as well as azo compounds such as azo-diisobutyric acid nitrile, which can be used, dissolved in solvents or volatile solvents such as dibutylphthalate, methanol, acetic ester, acetone or methylethyl ketone. The catalyst concentration in the solvents can be between 2 and 40%, preferably between 5 and 15%.

Catalyst systems which are designed to produce curing with a self-hardening action, in other words without additional use of heat, include an accelerator or activator in addition to the catalyst or initiator proper, said accelerator or activator causing the breakdown of the initiator and hence the initiation of the polymerization of the monomers to produce the polymers. Tertiary amines, alkyl amines, alkylacryl amines and oxyalkyl amines have proven satisfactory as such accelerators, as have reducing agents such as sulfinic acids or dithionites, added in amounts of 1–3%. Instead of the catalyst systems, naturally all other systems which can be used for polymerization of acrylates or methacrylates, for example those based on derivatives of mercaptans, mercaptides, acrylosulfonic alkylamines, etc., can be used. For example, paratoluolamine, in amounts of 0.5 to 2%, can be used as an accelerator. The accelerator according to the invention is preferably contained in the syrup or the paste itself. However, hardening can be initiated in the absence of the accelerator, essentially without or completely without the addition of heat under the influence of ultraviolet radiation. In hot polymerization, on the other hand, hardening is achieved by applying heat, for example without using an accelerator.

In the practical application of the materials according to the invention, for example for lining of prostheses, the polymer solution is mixed with a hardening catalyst dissolved in a solvent. This material is applied to the surface of the prosthesis which has previously been roughened, advantageously by dissolving it with a solvent such as methylmethacrylate; the material is then placed in the patient's mouth, where it polymerizes completely within several minutes under pressure and possibly with exclusion of air. When making repairs on dental prosthesis for example, it is advantageous to cover the material to be applied to this part with cellophane, since hardening should advantageously take place with exclusion of air. This also applies to the manufacture of dental fillings, artificial fingernails, etc. Hardening takes place even without covering with cellophane, but the latter gives a smoother and better surface.

When this material is used in dental medicine or dental technology, it has the great advantage that the finished polyacrylate solution can be caused to solidify in only a very short period of time by adding a catalyst solution, paste, or powder, and this material constitutes both the material used for making the impressions and the finished base material. In this manner, elastic, soft or permanently linings can be produced as desired, which are completely immune to the attack of bacteria and are absolutely resistant to mouth fluids, in addition to exhibiting a high resistance to abrasion and accuracy of fit.

The material according to the invention, which contains exclusively methacrylic acid esters or acrylic acid esters of 6-10 carbons as monomer components, will not cause burns, erosion, irritation or the like of the mucous membranes, even during cold polymerization, and the linings can be left in the mouth until they polymerize completely. This results in considerable permanence. Fitting old prostheses to the slightly changed jaw of the patient can be accomplished in a short period of time without high cost.

The materials according to the invention are especially suitable for dental purposes such as the manufacture of dental prostheses, their linings and repairs, used for taking impressions, filling teeth, and making dental replacements. However, they can also be used for other purposes such as making artificial fingernails or for plastic surgery on the ear, repairing hearing aids and the like, as well as for lining leg and arm prostheses and the like. Another area of application is the manufacture of eyeglass frames or the like.

The following examples are designed to illustrate the process in greater detail.

EXAMPLE 1a

A copolymer (25 parts by weight), consisting of 96 parts by weight of methyl methacrylate and 4 parts by weight ethylacrylate is mixed in a mixing vessel with 75 parts by weight of cyclohexyl acrylate, to which 1% p-toluolamine and 2%. 1,4-butane diol-dimethacrylate have been added. To this syrup, 2% of a commercial alkali aluminum silicate as well as 2.5% magnesium stearate is added.

To use this mixture, a solution of 5 parts by weight of benzoylperoxide in 25 parts by weight dibutylphthalate is added from a dropping bottle. After a short time, the material begins to become viscous, so that it can then be spread on the previously prepared prosthesis and inserted in the patient's mouth. After a few minutes, the material sets to form a hard lining.

EXAMPLE 1b

Instead of using the cycloalkylester, 65 parts by weight of a mixture of tertiary butyl methacrylate and epoxy-propyl-methacrylate in a ratio of 1:1 or 1:2 can be used, otherwise the process is the same as Example 1a.

EXAMPLE 2a

Starting with a solution of 35 parts by weight of a mixed polymer, composed of 60 parts by weight of methyl methacrylate and 40 parts by weight of ethyl acrylate in 65 parts by weight of ethyl hexyl methacrylate, 0.5% p-toluolamine and 1% 1,4-butane diol-dimethacrylate are added. Powdered magnesium stearate (1.5%) is then added to this material, and the solution mixed in a mixing vessel or on the prosthesis itself, with a solution of 10 parts by weight of benzoyl peroxide in 90 parts by weight ethyl acetate, dispensed from a dropping bottle. After a short time, the material becomes viscous, so that it can be spread on the prosthesis and placed in the patient's mouth. Here the material sets in 5 to 8 minutes, forming a permanently soft lining.

EXAMPLE 2b

Methacrylic acid n-hexyl ester in the same amount can be used instead of the ethyl hexyl methacrylate, otherwise the operation of Example 2a is followed.

EXAMPLE 3

A mixed polymer (50 parts) consisting of 96 parts by weight methyl methacrylate and 4 parts by weight methyl acrylate are dissolved in a mixture of 50 parts tertiary butyl methacrylate, methyl methacrylate, and n-hexyl methacrylate, mixed in a ratio of 1:1:1. Magnesium stearate (3%) and a commercial alkali aluminum silicate (1%) as well as 1% p-toluolamine are added to this material. As in Examples 1 and 2, a benzoyl peroxide solution is added dropwise to process the material, rapidly resulting in a viscous material which can be spread easily on the prosthesis and produces an elastic lining after a short space of time.

It will be obvious to those skilled in the art that various changes may be made without departing from the scope of the invention and the invention is not to be considered limited to what is described in the specification.

What is claimed is:
1. In a polymerizable composition for manufacturing elastic, soft, or hard plastic for dental and related purposes, comprising a mixture of at least one acrylate or methacrylate polymer or copolymer in at least one acrylate or methacrylate monomer, and at least one additive, the improvement wherein:
said composition further contains a metal soap component present in an amount sufficient to improve dimensional stability and surface quality.
2. A composition according to claim 1, further comprising a metal silicate.

3. A composition according to claim 1 or 2, said monomeric acrylic or methacrylic acid ester comprising a methyl ester.

4. A composition according to claim 1 or 2, said monomeric acrylic or methacrylic acid ester comprising predominantly an ester having 6 to 10 carbon atoms.

5. A composition according to claim 4, wherein the monomeric acrylic or methacrylic acid ester is a t-butyl ester, epoxy-propyl ester hexyl ester or a mixture thereof.

6. A composition according to claim 5, wherein said ester is a cyclohexyl ester.

7. A composition according to claim 1, wherein said monomeric acrylic or methacrylic acid ester, which serves for dissolving or dispersing the polymer component, constitutes at least partially a cross-linking dimethacrylate.

8. A composition according to claim 7, wherein the monomeric acrylic or methacrylic acid ester, which serves to dissolve or disperse the polymer component, completely constitutes said cross-linking agent.

9. A composition according to claim 7, wherein the cross-linking dimethacrylate is an olefinic dimethacrylate or a (poly)ethylene glycol dimethacrylate.

10. A composition according to claim 4, wherein the polymer is a mixture of polymethacrylates of medium molecular weight.

11. A composition according to claim 4, wherein the polymer is a mixture of at least one polymethacrylate of medium molecular weight and at least one polyacrylate.

12. A composition according to claim 4, wherein the amount by weight of the polymer is 10 to 40%, based on the total mass.

13. A composition according to claim 2, wherein the metal silicate is an alkali metal silicate.

14. A composition according to claim 2, wherein the amount of said at least one of the metal soap or the silicate is 0.1 to 10% by weight based on the total amount.

15. A composition according to claim 2, wherein the amount of said at least one of the metal soap or the silicate is 1.5 to 5% by weight.

16. A composition according to claim 1, wherein the metal soap is at least one alkaline earth fatty acid salt.

17. A composition according to claim 1, wherein the metal soap is calcium stearate or magnesium stearate or a mixture thereof.

18. A composition according to claim 2, wherein the metal silicate is an alkali aluminum silicate.

19. Use of the composition according to claim 4 for the manufacture of plastic dental prostheses, dental replacements, teeth, jaw impressions, or linings for prostheses comprising adding a catalyst to said composition, and placing said composition in the mouth for polymerization in situ.

20. Use of the material according to claim 19, whereby the catalyst is applied separately in a rapidly evaporating solvent or a primer film upon a tooth cavity or the underside of the prosthesis after preliminary roughening of the adhesive surface of the prosthesis or on the jaw side either alone or with the addition of a catalyst to the material.

21. Use of the material according to claim 1 for the manufacture of linings for limb prostheses.

22. Use of the material according to claim 1 for the manufacture of artificial fingernails.

* * * * *